(12) United States Patent
Vizard et al.

(10) Patent No.: US 7,734,325 B2
(45) Date of Patent: Jun. 8, 2010

(54) APPARATUS AND METHOD FOR MULTI-MODAL IMAGING

(75) Inventors: Douglas L. Vizard, Durham, CT (US);
Joel N. Helfer, Cheshire, CT (US);
George Brocksieper, Guilford, CT (US); William E. Mclaughlin, Guilford, CT (US)

(73) Assignee: Carestream Health, Inc., Rochester, NY (US)

( * ) Notice: Subject to any disclaimer, the term of this patent is extended or adjusted under 35 U.S.C. 154(b) by 783 days.

(21) Appl. No.: 11/221,530

(22) Filed: Sep. 8, 2005

(65) Prior Publication Data

US 2006/0064000 A1   Mar. 23, 2006

Related U.S. Application Data

(60) Provisional application No. 60/611,841, filed on Sep. 21, 2004.

(51) Int. Cl.
*A61B 6/00* (2006.01)

(52) U.S. Cl. ............... 600/407; 600/425; 600/436; 600/476; 378/51; 382/131; 250/339.06; 250/336.1; 250/367

(58) Field of Classification Search ............... 600/407, 600/440, 425, 436, 476; 382/131; 250/339.06, 250/336.1, 367; 378/51
See application file for complete search history.

(56) References Cited

U.S. PATENT DOCUMENTS 5,717,791 A * 2/1998 Labaere et al. ............ 382/274
5,748,768 A * 5/1998 Sivers et al. ............... 382/130
6,269,177 B1 * 7/2001 Dewaele et al. ............ 382/131
6,346,707 B1   2/2002 Vizard et al.

(Continued)

FOREIGN PATENT DOCUMENTS

EP   1 111 625 A2   6/2001

(Continued)

OTHER PUBLICATIONS

Kodak Image Station 2000MM Multimodal Imaging System, Internet web address: http://www.kodak.com/US/en/health/scientific/products/imgStation2000MM/index.shtml, Sep. 16, 2004.

(Continued)

*Primary Examiner*—Long V Le
*Assistant Examiner*—Vani Gupta

(57) ABSTRACT

An imaging system for imaging an object. The imaging system includes a support member adapted to receive the object in an immobilized state. The system also includes first means for imaging the immobilized object in a first imaging mode to capture a first image, and second means for imaging the immobilized object in a second imaging mode, different from the first imaging mode, to capture a second image. The first imaging mode is selected from the group: x-ray mode and radio isotopic mode. The second imaging mode is selected from the group: bright-field mode and dark-field mode. A removable phosphor screen is employed when the first image is captured and not employed when the second image is captured. The phosphor screen is adapted to transduce ionizing radiation to visible light. The phosphor screen is adapted to be removable without moving the immobilized object. The system can further include means for generating a third image comprised of the first and second image.

10 Claims, 8 Drawing Sheets

U.S. PATENT DOCUMENTS

| | | | |
|---|---|---|---|
| 6,444,988 B1 | 9/2002 | Vizard | |
| 6,459,094 B1* | 10/2002 | Wang et al. | 250/584 |
| 2001/0012386 A1* | 8/2001 | Struye et al. | 382/131 |
| 2004/0202360 A1* | 10/2004 | Besson | 382/131 |

FOREIGN PATENT DOCUMENTS

| | | |
|---|---|---|
| WO | 2004/081865 A2 | 9/2004 |

OTHER PUBLICATIONS

"The Bare Bones of Animal Imaging", Linda Sage, *The Scientist*, vol. 19, Issue 4, p. 36, Feb. 28, 2005.

"Research Takes Many Directions", The Scientist, vol. 303, No. 5657, single page Kodak ad, Jan. 23, 2004.

CosmoBio report, Mar. 2004, No. 43, "Kodak Image Station 2000MM" (English translation).

CosmoBio report, Mar. 2004, No. 43, "Kodak Image Station 2000MM" (foreign).

User's Guide for 2000R (172 pages), 2001-2002.

User's Guide for 2000MM (168 pages), 2003.

"The Bare Bones of Animal Imaging", Linda Sage, *The Scientist*, vol. 19, Issue 4, p. 36, Feb. 28, 2005.

"Research Takes Many Directions", The Scientist, vol. 303, No. 5657, single page Kodak ad, Jan. 23, 2004.

CosmoBio report, Mar. 2004, No. 43, "Kodak Image Station 2000MM" (English translation).

CosmoBio report, Mar. 2004, No. 43, "Kodak Image Station 2000MM" (foreign).

User's Guide for 2000R (172 pages).

User's Guide for 2000MM (168 pages).

Kodak Image Station 2000MM Multimodal Imaging System, Internet web address: http://www.kodak.com/US/en/health/scientific/products/imgStation2000MM/index.shtml.

* cited by examiner

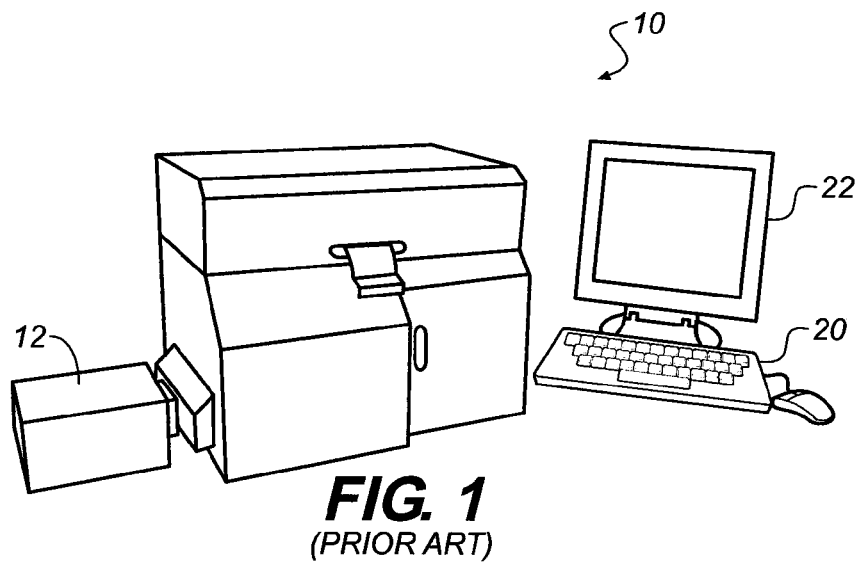
FIG. 1
(PRIOR ART)
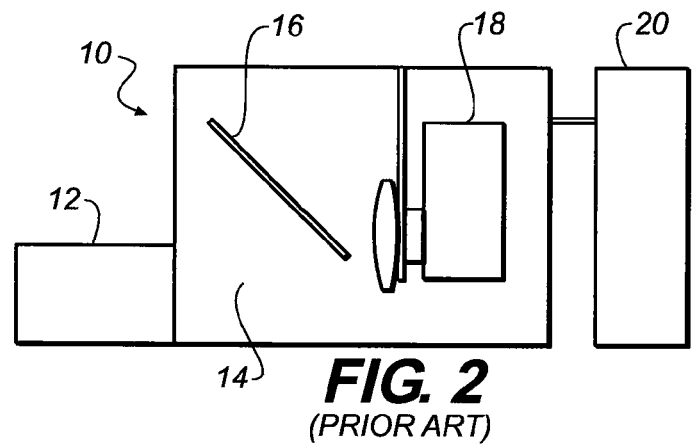
FIG. 2
(PRIOR ART)
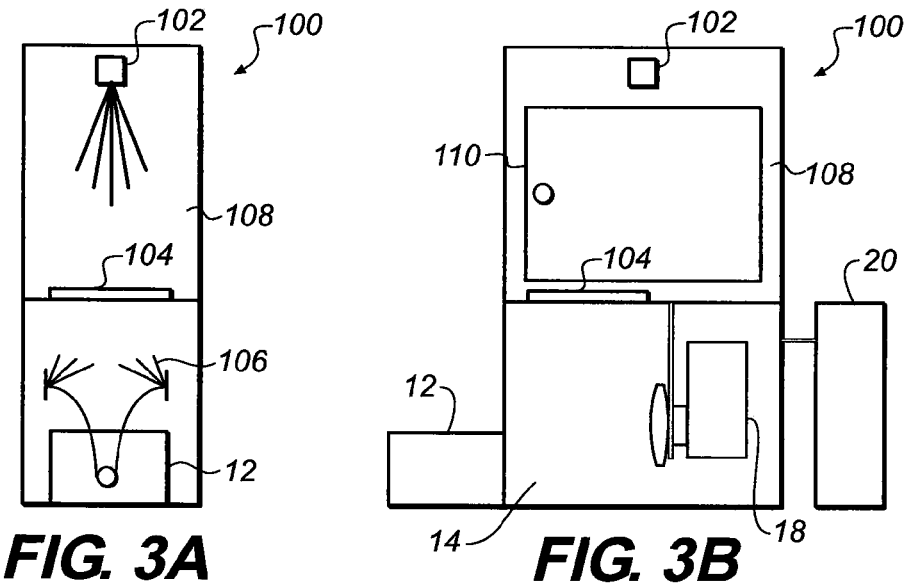
FIG. 3A    FIG. 3B

APPARATUS AND METHOD FOR MULTI-MODAL IMAGING

CROSS REFERENCE TO RELATED APPLICATIONS

Reference is made to commonly assigned Provisional U.S. Patent Application No. 60/611,841, entitled "APPARATUS AND METHOD FOR MULTI-MODAL IMAGING", and filed on Sep. 21, 2004 in the names of Vizard et al., and which is assigned to the assignee of this application, and incorporated herein by reference.

FIELD OF THE INVENTION

The invention relates generally to the field of imaging systems, and more particularly to the imaging of objects. More specifically, the invention relates to an apparatus and method that enable analytical imaging of objects (for example, small animals and tissue) in differing modes, including bright-field, dark-field (e.g., luminescence and fluorescence), and x-ray and radioactive isotopes.

BACKGROUND OF THE INVENTION

Electronic imaging systems are well known for enabling molecular imaging. An exemplary electronic imaging system (shown in FIG. 1 and diagrammatically illustrated in FIG. 2) is the Image Station 2000MM Multimodal Imaging System 10 available from the Eastman Kodak Company. System 10 includes a light source 12, an optical compartment 14 which can include a mirror 16, a lens/camera system 18, and a communication/computer control system 20 which can include a display device, for example, a computer monitor 22. Camera/lens system 18 can include an emission filter wheel for fluorescent imaging. Light source 12 can include an excitation filter selector for fluorescent excitation or bright field color imaging. In operation, an image of an object is captured using lens/camera system 18. System 18 converts the light image into an electronic image, which can be digitized. The digitized image can be displayed on the display device, stored in memory, transmitted to a remote location, processed to enhance the image, and/or used to print a permanent copy of the image.

Applicants have recognized a need for an apparatus and method for enabling analytical imaging of an object in differing modes.

SUMMARY OF THE INVENTION

An object of the present invention is to provide an apparatus and method for enabling analytical imaging of an object.

Another object of the present invention is to provide such an apparatus and method for enabling analytical imaging of an object in differing modes.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided an imaging system for imaging an object. The imaging system includes a support member adapted to receive the object in an immobilized state. The system also includes first means for imaging the immobilized object in a first imaging mode to capture a first image, and second means for imaging the immobilized object in a second imaging mode, different from the first imaging mode, to capture a second image. The first imaging mode is selected from the group: x-ray mode and radio isotopic mode. The second imaging mode is selected from the group: bright-field mode and dark-field mode. A removable phosphor screen is employed when the first image is captured and not employed when the second image is captured. The phosphor screen is adapted to transduce ionizing radiation to visible light. The phosphor screen is adapted to be removable without moving the immobilized object. The system can further include means for generating a third image comprised of the first and second image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1 shows a perspective view of an exemplary prior art electronic imaging system.

FIG. 2 shows a diagrammatic view of the prior art electronic imaging system of FIG. 1.

FIG. 3A shows a diagrammatic side view of the imaging system in accordance with the present invention.

FIG. 3B shows a diagrammatic front view of the imaging system of FIG. 3A.

DETAILED DESCRIPTION OF THE INVENTION

Figure 4:
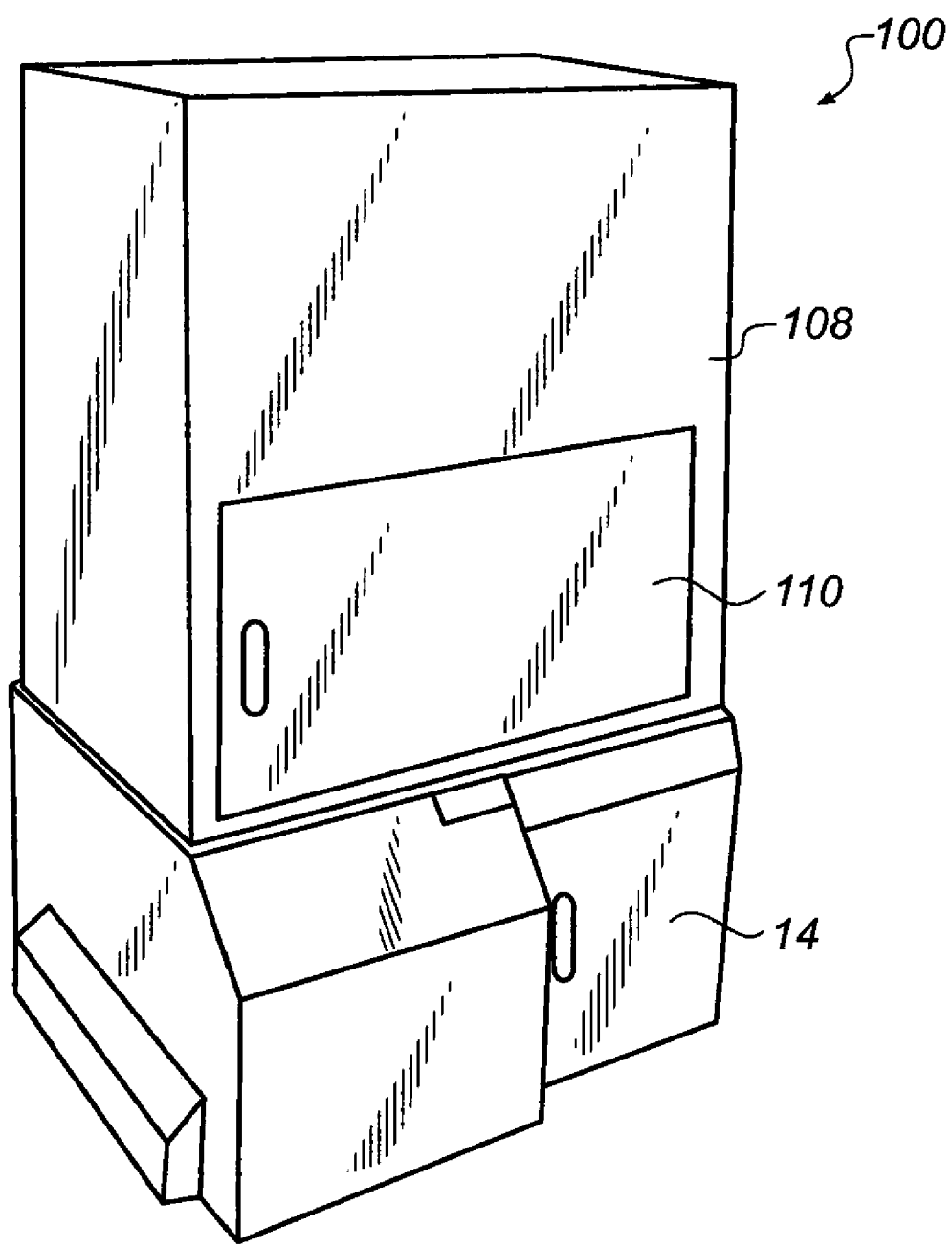
FIG. 4 shows a perspective view of the imaging system of FIGS. 3A and 3B.

The following is a detailed description of the preferred embodiments of the invention, reference being made to the drawings in which the same reference numerals identify the same elements of structure in each of the several figures.

Applicants have recognized that the complex pharmaceutical analyses of small objects/subjects (e.g., small animal and tissue) images are particularly enhanced by using different in-vivo imaging modalities. Using the known/current practices of bright-field, dark-field and radiographic imaging for the analysis of small objects/subjects (such as a mouse) can be expensive and may not provide the precision of co-registered images that is desired.

Using the apparatus and method of the present invention, precisely co-registered fluorescent, luminescent and/or isotopic probes within an object (e.g., a live animal and tissue) can be localized and multiple images can be accurately overlaid onto the simple bright-field reflected image or anatomical x-ray of the same animal within minutes of animal immobilization.

The present invention uses the same imaging system to capture differing modes of imaging, thereby enabling/simplifying multi-modal imaging. In addition, the relative movement of probes can be kinetically resolved over the time period that the animal is effectively immobilized (which can be tens of minutes). Alternatively, the same animal may be subject to repeated complete image analysis over a period of days/weeks required to assure completion of a pharmaceutical study, with the assurance that the precise anatomical frame of reference (particularly, the x-ray) may be readily reproduced upon repositioning the object animal. The method of the present invention can be applied to other objects and/or complex systems subject to simple planar imaging methodologies.

More particularly, using the imaging system of the present invention, an immobilized object can be imaged in several imaging modes without changing/moving the immobilized object. These acquired multi-modal images can then be merged to provide one or more co-registered images for analysis.

Imaging modes supported by the apparatus/method of the present invention include: x-ray imaging, bright-field imaging, dark-field imaging (including luminescence imaging, fluorescence imaging) and radioactive isotope imaging. Images acquired in these modes can be merged in various combinations for analysis. For example, an x-ray image of the object can be merged with a near IR fluorescence image of the object to provide a new image for analysis.

The apparatus of the present invention is now described with reference to FIGS. 3A, 3B, and 4. FIG. 3A shows a diagrammatic side view of an imaging system 100 in accordance with the present invention, FIG. 3B shows a diagrammatic front view of imaging system 100, and FIG. 4 shows a perspective view of imaging system 100.

Imaging system 100 includes light source 12, optical compartment 14, a lens/camera system 18, and communication/computer control system 20 which can include a display device, for example, a computer monitor 22. Camera/lens system 18 can include an emission filter wheel for fluorescent imaging. Light source 12 can include an excitation filter selector for fluorescent excitation or bright field color imaging.

As best shown in FIG. 3A, imaging system 100 includes an x-ray source 102 and a support member such as a sample object stage 104. An immobilized object such as a mouse is received on and supported by sample object stage 104 during use of system 100. Imaging system 100 further comprises epi-illumination, for example, using fiber optics 106, which directs conditioned light (of appropriate wavelength and divergence) toward sample object stage 104 to provide bright-field or fluorescent imaging.

Sample object stage 104 is disposed within a sample environment 108, which allows access to the object being imaged. Preferably, sample environment 108 is light-tight and fifed with light-locked gas ports (not illustrated) for environmental control. Environmental control enables practical x-ray contrast below 8 Kev (air absorption) and aids in life support for biological specimens. Such environmental control might be desirable for controlled x-ray imaging or for support of particular specimens.

Imaging system 100 can include an access means/member 110 to provide convenient, safe and light-tight access to sample environment 108, such as a door, opening, labyrinth, and the like. Additionally, sample environment 108 is preferably adapted to provide atmospheric control for sample maintenance or soft x-ray transmission (e.g., temperature/humidity/alternative gases and the like).

Imaging system 100 can be a unitary system. Alternatively, imaging system 100 can be a modular unit adapted to be used/mated with electronic imaging system such as electronic imaging system 10.

Figure 5A:
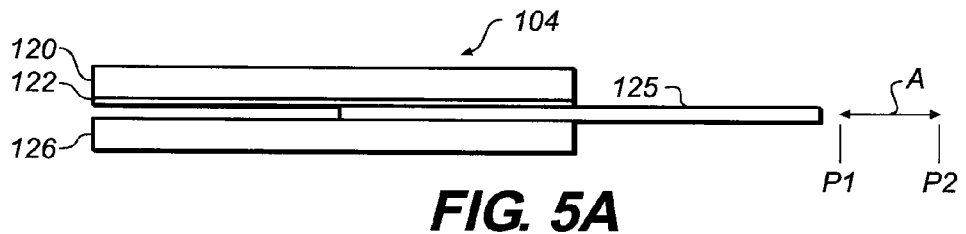
FIG. 5A shows a diagrammatic side view of the sample object stage.
Figure 5B:
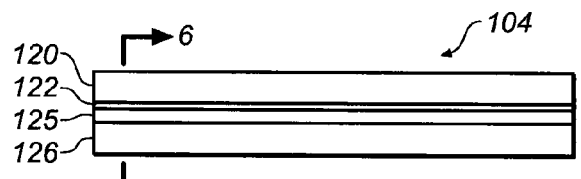
FIG. 5B shows a diagrammatic side view of the sample object stage in the first imaging position P1 wherein the phosphor plate is disposed proximate the sample object stage.
Figure 5C:
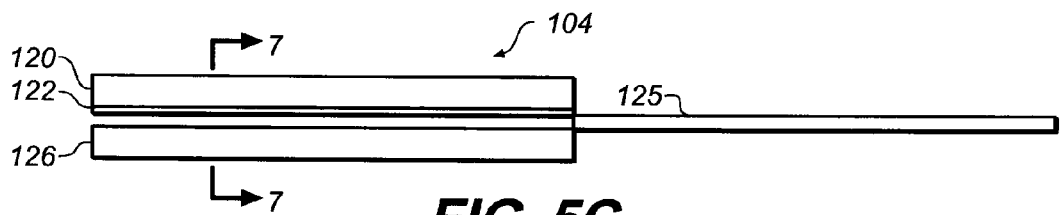
FIG. 5C shows a diagrammatic side view of the sample object stage in the second imaging position P2 wherein the phosphor plate is not proximate the sample object stage.
Figure 6:
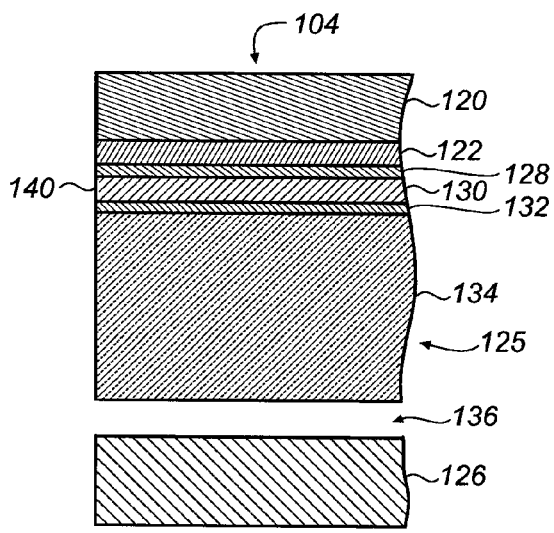
FIG. 6 shows an enlarged, fragmentary sectional view taken along line 6-6 of FIG. 5B.
Figure 7:
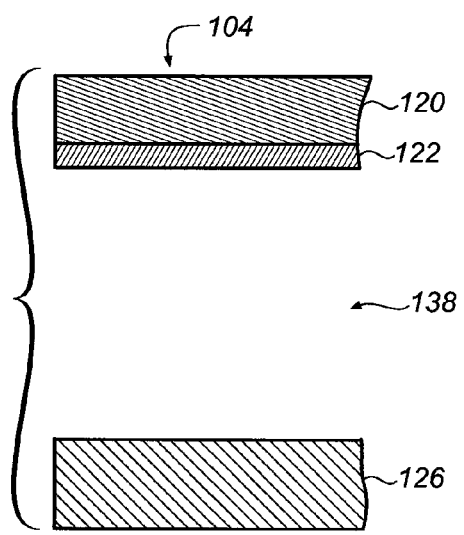
FIG. 7 shows an enlarged, fragmentary sectional side view taken along line 7-7 of FIG. 5C.

FIGS. 5-7 more particularly illustrate elements of sample object stage 104 and an optical interface relative with the focal plane of camera/lens system 18. FIG. 5A shows a diagrammatic side view of sample object stage 104 showing the relative movement of a movable phosphor plate 125 according to the invention relative to the sample object stage. FIG. 5B shows a diagrammatic side view of the sample object stage in a first imaging position P1 wherein phosphor plate 125 is disposed proximate the sample object stage and positioned for imaging light from a phosphor layer 132, shown in FIG. 6. FIG. 5C shows a diagrammatic side view of the sample object stage in the second imaging position P2 wherein phosphor plate 125 has been withdrawn to a position that is not proximate the sample object stage. FIG. 6 shows an enlarged, fragmentary sectional view taken along line 6-6 of FIG. 5B, which corresponds with the first imaging position P1. FIG. 7 shows an enlarged, fragmentary sectional view taken along line 7-7 of FIG. 5C, which corresponds with the second imaging position P2.

Continuing with regard to FIGS. 6 and 7, sample object stage 104 includes a support member made up from an open frame 120 to support and stretch a thin plastic support sheet 122. Support sheet 122 is selected so as to support the weight of a sample or object to be imaged and is made from a material that is optically clear and free of significant interfering fluorescence.

Phosphor plate 125 is mounted for motion toward and away from sample object stage 104. While those skilled in the art might recognize other configurations, in a preferred embodiment, phosphor plate 125 is mounted for translation to provide slidable motion (in the direction of arrow A in FIG. 5A) relative to frame 120, beneath the sample, in intimate contact with support sheet 122. Such motion can be accomplished using methods known to those skilled in the art, for example, frame 100 and phosphor plate 125 can be disposed on rails supported by a surface of an optical platen 126. As will be more particularly described below, in first imaging position P1, phosphor layer 130 in phosphor plate 125 is in overlapping arrangement with sample object stage 104 (FIG. 6) when an x-ray image of the object is captured. In second imaging position P2, phosphor plate 125 is translated/moved away from sample object stage 104 (FIG. 7) for capture of an image of the object such that phosphor plate 125 is not imaged when an image of the object is captured in second imaging position P2.

FIG. 6 provides an enlarged view of sample object stage 104 including phosphor plate 125 to more particularly show a focal plane Sample support sheet 122 preferably comprises Mylar or polycarbonate and has a nominal thickness of about 0.1 mm. A protective layer 128 (for example, reflective Mylar) of about 0.025 mm is provided on phosphor layer 130 to protect the surfaces of layer 130 during movement of phosphor plate 125. Protective layer 128 promotes/increases the image-forming light output. In a preferred embodiment, protective layer 128 is reflective so as to prevent object reflection back into the image-forming screen, reducing the confusing the ionizing radiation image.

Phosphor layer 130 functions to transduce ionizing radiation to visible light practically managed by lens and camera system 18 (such as a CCD camera). Phosphor layer 130 can have thickness ranging from about 0.01 mm to about 0.1 mm, depending upon the application (i.e., soft x-ray, gamma-ray or fast electron imaging). On the underside of phosphor layer 130, as illustrated, an optical layer 132 is provided for conditioning emitted light from phosphor layer 130. Optical layer 132 can have a thickness in the range of less than about 0.001 mm. Particular information about phosphor layer 130 and optical layer 132 is disclosed in U.S. Pat. No. 6,444,988 (Vizard), commonly assigned and incorporated herein by reference. A supporting glass plate 134 is provided. Glass plate 134 is spaced at a suitable mechanical clearance from an optical platen 126, for example, by an air gap/void 136. In the preferred embodiment, the surfaces of clear optical media (e.g., a lower surface of glass plate 134 and both surfaces of optical platen 126) are provided with anti-reflective coating to minimize reflections that may confuse the image of the object.

FIG. 7 provides an expanded view of sample object stage 13 including wherein phosphor plate 125 is removed (i.e., taken along line 7-7 of FIG. 5C). As shown in FIG. 7 is frame 120, sample support sheet 122, an air gap/void 138 (since phosphor plate 125 is removed), and optical platen 126.

Figure 8:
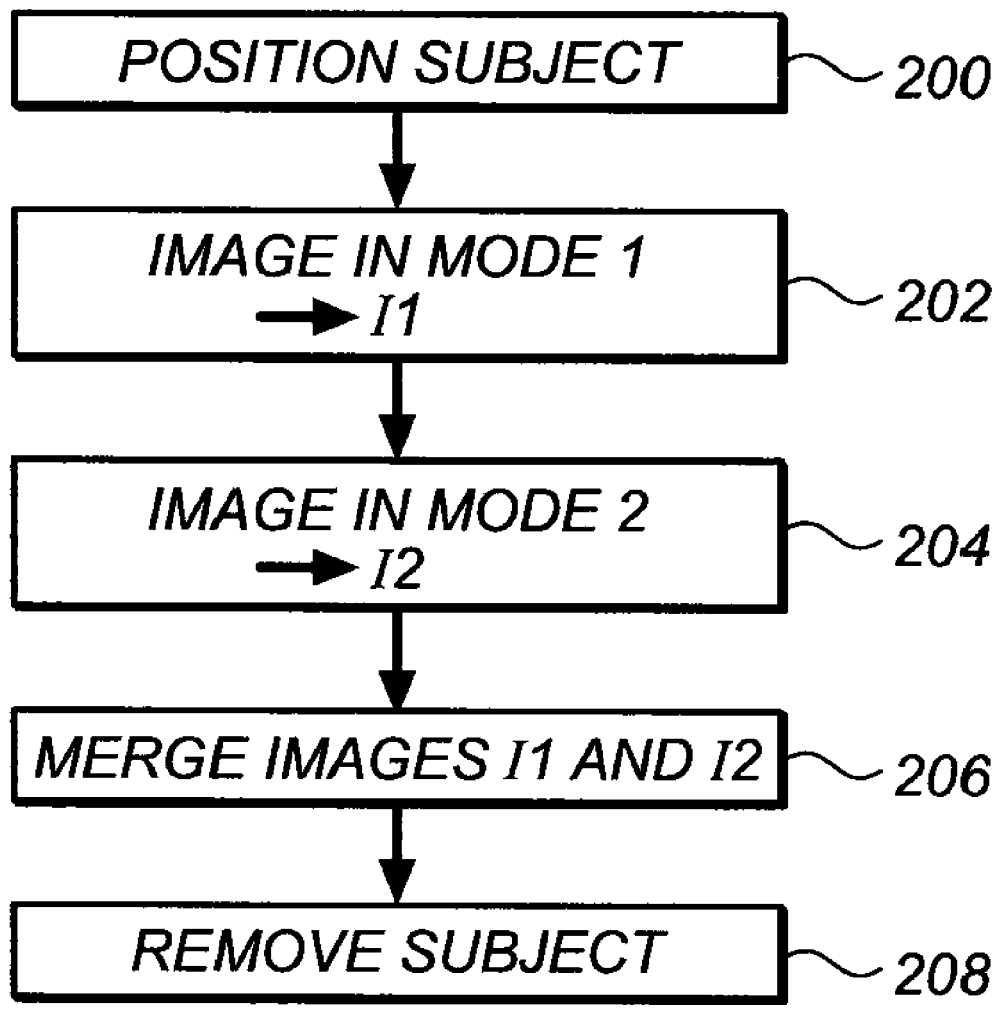
FIG. 8 shows a work flow diagram in accordance with a method of the present invention.

Referring now to FIG. 8, in operation, an object (such as a small animal) is immobilized on sample object stage 104 (step 200). An operator configures system 100 for imaging in a first mode, and an image of the object is captured using lens/camera system 18 in the first mode (step 202). System 18 converts the light image into an electronic image which can be digitized. This digitized image is referred to as Image1 or I1. The digitized image can be displayed on the display device, stored in memory, transmitted to a remote location, processed to enhance the image, and/or used to print a permanent copy of the image. The object remains immobilized on sample object stage 104; no change in the position/location of the object is made. The operator configures system 100 for imaging in a second mode (step 204), and an image of the object is captured using lens/camera system 18 in the second mode. The resulting digitized image is referred to as Image2 or I2. Since the position of the object was not moved/changed during the capture of the images, both Image1 and Image2 can readily be merged or superimposed, using methods known to those skilled in the art, such that the two images are co-registered. As such, a third image can be generated comprising Image1 and Image2.

As indicated above, system 100 can be configured in several modes, including: x-ray imaging, bright-field imaging, dark-field imaging (including luminescence imaging, fluorescence imaging) and radioactive isotope imaging. To configure system 100 for x-ray imaging or isotope imaging, phosphor plate 125 is moved to position P1 in optical registration with sample object stage 104 (as shown in FIGS. 5B and 6). For an x-ray image, x-ray source 102 is employed when capturing the image of the immobilized object. To configure system 100 for bright-field imaging or dark-field imaging (including luminescence imaging and fluorescence imaging) without moving the immobilized object and the support member or object stage, phosphor plate 125 is moved to position P2, out of optical registration with sample object stage 104 (as shown in FIGS. 5C and 7), and an image of the immobilized object is appropriately captured. The object is immobilized on sample object stage 104, and light emitted from the object (usually diffusive within the turbid constituents of a solid object) is projected to the object surface, which intimately bears upon the upper surface of sample support sheet 122.

For the purpose of optical imaging, the object surface is defined by a refractive boundary (e.g., the skin of an animal) that delineates the interior of the object (usually a heterogeneous, turbid media of higher index of refraction) and air. Light emanating from within an object (e.g., luminescent or transmitted) projects to the surface from which it scatters, defining the light that may be productively managed to create an image of the object. Conversely, light may be provided from beneath optical platen 126 and scattered from the object surface, thereby providing reflective light for imaging the same object.

For optical imaging, the definition of the object boundary may be moderated by matching the refractive index of the object boundary to support sheet 122 by introducing an index-matching fluid (e.g., water). The depth to which good focus can be achieved in optical imaging is dependent on minimizing the surface scatter of the object, and methods such as index matching and increasing wavelength (e.g., near-infrared, NIR imaging) are is well known in the art.

The depth to which good focus can be achieved in optical imaging is dependent on minimizing the surface scatter of the object, and methods such as index matching and increasing wavelength (e.g., near-infrared, NIR imaging) are well known in the art.

The emitted sample light can arise from luminescence, fluorescence or reflection, and the focal plane of the lens can be adjusted to the elevation of object surface. Alternatively, the "light" can be ionizing radiation passing through or emitted from the object, or passing into the phosphor and forming an image. Soft x-rays, consistent with thin objects or small animals, project an image through the diffusive phosphor onto the optical boundary, adding the depth of the phosphor (more than about 0.02 mm) to the depth of focus. More significant is the focal distance contributed by the phosphor support plate 134, which may be fractional millimeters, depending upon the thickness and index of the glass or plastic. The fractional-millimeter elevation of the best focal plane contributed by the phosphor support can provide a better coincidence between the phosphor focal plane and the focal plane used for optical imaging. For near infrared (NIR) optical imaging, the preferred/best focal plane may be located at millimeter depths into a nominally turbid object. The phosphor support plate 134 can be thicker to maximize the coincidence of the optical and phosphor imaging planes. Those skilled in the art will recognize how to tune the materials of the present invention to optimally co-locate the preferred optical and phosphor imaging planes. Currently described materials may be practically assembled to assure multi-modal focal plane co-location to accommodate the demands of a fast lens system.

Appropriately fast lens systems for dark-field and x-ray imaging applications will likely have sub-millimeter focal depths, necessitating the above considerations. Accordingly, for a particular embodiment, it may be desirable for multiple optical elements to enable the location of a common focal plane shared by differing modes of imaging.

Emitted gamma rays from a thick object (such as 99Tc emission from an animal organ) are distributed over the plane of the phosphor, diffusing the image by millimeters, and an appropriately thick phosphor layer (about 0.1 mm) may be preferred for increased detection efficiency. Consequently, the location of the focal plane at the supporting sheet is not critical to the resolution of the radio isotopic image. Better resolution and more precise planar projection of the emitting isotope can be achieved by gamma-ray collimation. Collimators of millimeter-resolution are available and capable of projecting isotopic location to millimeter resolution at the focal plane of the phosphor in the present invention.

Of particular relevance to the operation of the present invention is the thickness of the layers in the focal plane of the lens. For example, fast lenses, (which are essential elements for the practice of imaging low-light emissions) will have a focal depth of focus of about 0.5 mm for very fast lenses. For good resolution of objects of interest, less than about 0.2 mm of spatial resolution is desirable, and a megapixel CCD camera (cooled) imaging at 100 mm field is suitable. Generally, more resolution is desirable.

Precision registration of the multi-modal image can be accomplished using methods known to those skilled in the art. By placing the object on a thin, stretched optical support that allows phosphor plate 125 to be removed without displacement of the object, co-registered optical imaging is enabled by the same lens/camera system using epi-illumination methodologies at a sufficiently similar focal plane.

Examples are now provided.

Figure 9A:
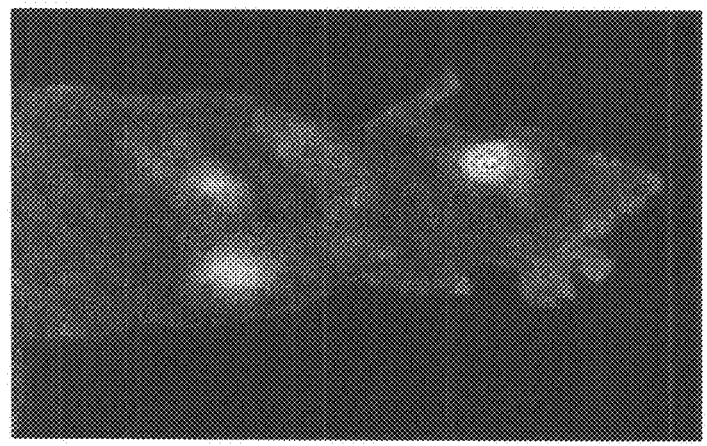
FIG. 9A shows a first image of an immobilized object in a first imaging mode.
Figure 9B:
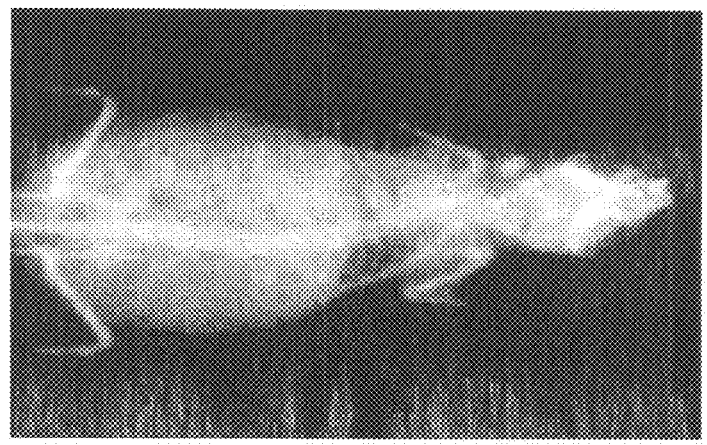
FIG. 9B shows a second image of the immobilized object of FIG. 9A in a second imaging mode.
Figure 9C:
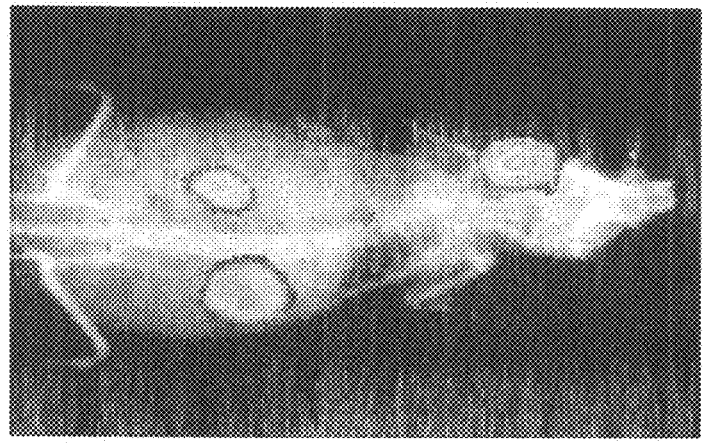
FIG. 9C shows an image generated by the merger of the images of FIGS. 9A and 9B.

FIGS. 9A-9C show images captured using the apparatus and method of the present invention. A mouse was immobilized on sample object stage 104 (step 200 of FIG. 8) of system 100. System 100 was first configured for NIR fluorescence imaging wherein phosphor plate 125 is removed from co-registration with frame 100. A first image was captured and is displayed in FIG. 9A (step 202 of FIG. 8). Next, system 100 was configured for x-ray imaging wherein phosphor plate 125 is placed in co-registration with frame 100. A second image was captured and is displayed in FIG. 9B (step 204 of FIG. 8). Using methods known to those skilled in the art, the first and second images were merged (step 206 of FIG. 8) and the merged image is displayed in FIG. 9C. Note that the fluorescent signals superimposed on the anatomical reference clarify the assignment of signal to the bladder and an expected tumor in the neck area of this illustrated experimental mouse.

It is noted that the first and/or second image can be enhanced using known image processing methods/means prior to be merged together. Alternatively, the merged image can be enhanced using known image processing methods/ means. Often, false color is used to distinguish fluorescent signal from gray-scale x-rays in a merged image.

Figure 10C:
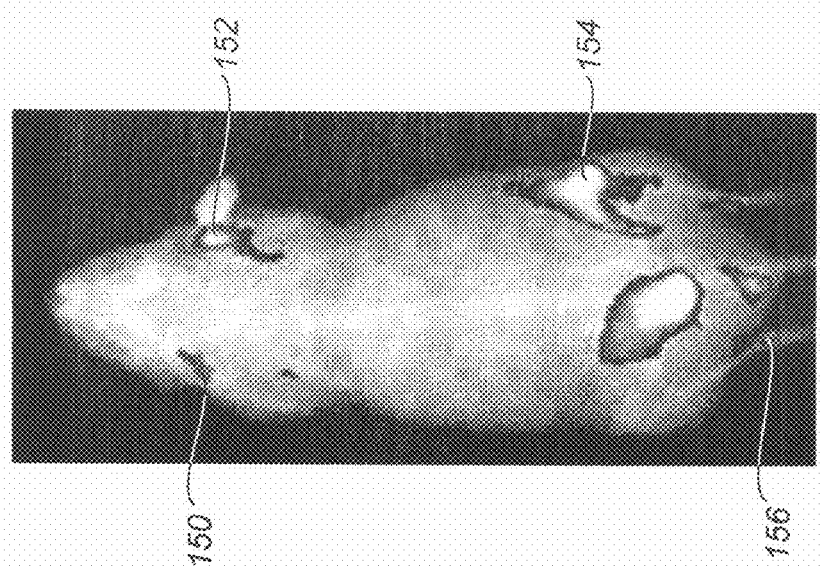
FIG. 10C shows an image generated by the merger of the images of FIGS. 10A and 10B.
Figure 10B:
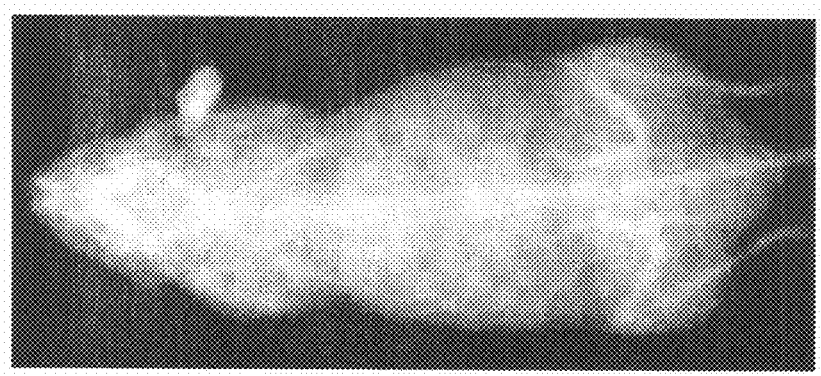
FIG. 10B shows a second image of the immobilized object of FIG. 10A in a second imaging mode.
Figure 10A:
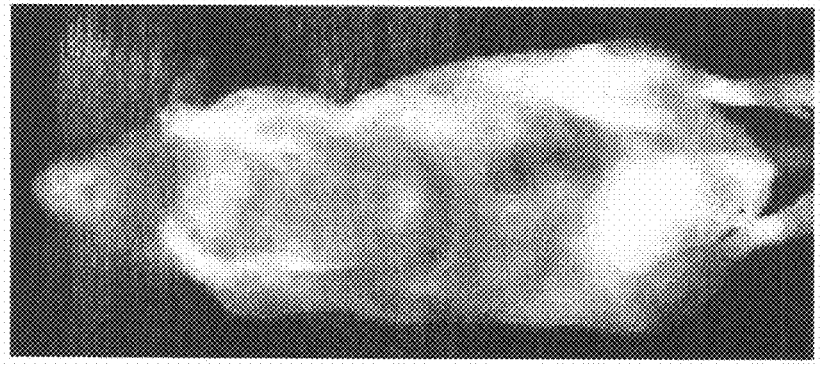
FIG. 10A shows a first image of an immobilized object in a first imaging mode.

FIGS. 10A-10C provide a further example using the apparatus and method of the present invention. FIG. 10A is a NIR fluorescence image of a mouse while FIG. 10B is an x-ray image of the same immobilized mouse. Using methods known to those skilled in the art, the first and second images were merged and the merged image is displayed in FIG. 10C.

Prior to being merged, the first and second images were contrasted. This processing allows particular areas of the mouse to be visually enhanced for diagnostic purposes. For example, areas 150, 152, and 156 are potential secondary early detection sites, and area 154 shows the primary tumor injection site at the knee.

Figure 11A:
FIG. 11A shows a first image of an immobilized object in a first imaging mode.
Figure 11B:
FIG. 11B shows a second image of the immobilized object of FIG. 11A in a second imaging mode.
Figure 11C:
FIG. 11C shows an image generated by the merger of the images of FIGS. 11A and 11B.

FIGS. 11A-11C provide yet a further example using the apparatus and method of the present invention. FIG. 11A is a near IR fluorescence image of a mouse wrist while FIG. 11B is an x-ray image of the same immobilized mouse wrist. Using methods known to those skilled in the art, the first and second images were merged and the merged image is displayed in FIG. 11C. The merged image provides a diagnostic image for viewing a potential secondary tumor site. Note that this image set clearly demonstrates the precision to which the current invention enables the co-location of objects from differing imaging modes. The maximum fluorescent signal emanating from a pre-metastatic tumor on the radius (arm-bone) tip at the wrist is within about 0.1 mm of the suspect lesion subsequently identified by microscopic histology.

Figure 12:
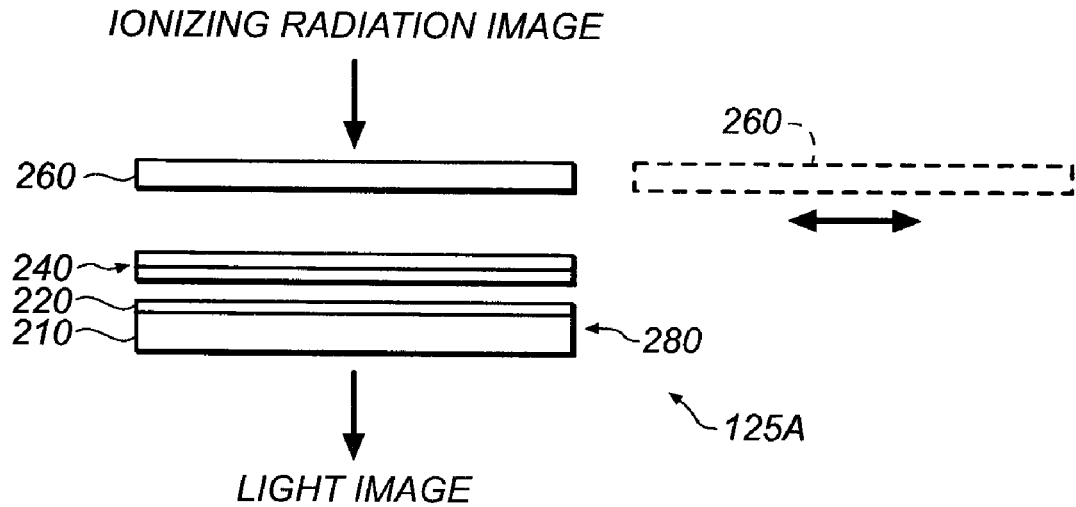
FIG. 12 is a diagrammatic view of a suitable phosphor plate for use with the apparatus and method of the present invention.

A phosphor plate suitable for use with the apparatus and method of the present invention is disclosed in U.S. Pat. No. 6,444,988 (Vizard), commonly assigned and incorporated herein by reference. A phosphor plate as described in Vizard is shown in FIG. 12. A suitable phosphor plate 125A for use with the apparatus and method of the present invention includes a transparent support 210 (such as glass) upon which is coated an interference filter 220 which is a multicoated short-pass filter designed to transmit light at a specified wavelength (and below) and reflect light above that wavelength. Plate 125A also includes a thin phosphor layer 240 and a removable thick phosphor layer 260. Thin phosphor layer 240 is used for high resolution imaging applications of ionizing radiation or for very low energy (self-attenuating) ionizing radiation such as low-energy electrons or beta particles. Thick phosphor layer 260 is used for high energy ionizing radiation that freely penetrates the phosphor. Thick phosphor layer 260 is removable and is shown in FIG. 12 overlaying thin phosphor layer 240. Layer 260 is removable to the position shown in dashed lines out of contact with layer 240.

The phosphor preferably used in phosphor layers 240 and 260 is Gadolinium Oxysulfide: Terbium whose strong monochromatic line output (544-548 nanometers (NM) is ideal for co-application with interference optics. This phosphor has technical superiority regarding linear dynamic range of output, sufficiently "live" or prompt emission and time reciprocity, and intrascenic dynamic range which exceed other phosphors and capture media. This phosphor layer preferably has a nominal thickness of 10-30 micrometers (μm) at 5-20 grams/square foot (g/ft2) of phosphor coverage, optimally absorbing 10-30 Kev x-rays. Thick phosphor layer 260 has a nominal thickness of 100 μm at 80 g/ft2 of phosphor coverage.

The duplex phosphor layers impart flexibility of usage for which the thick phosphor layer 260 may be removed to enhance the spatial resolution of the image. Thin phosphor layer 240 intimately contacts filter 220, whereas thick phosphor layer 260 may be alternatively placed on thin phosphor layer 240.

Interference filter 220 transmits light at 551 NM and below and reflects light above that wavelength. Filter 220 comprises layers of Zinc Sulfide-Cryolite that exhibits a large reduction in cutoff wavelength with increasing angle of incidence. The filter has a high transmission at 540-551 NM to assure good transmission of 540-548 NM transmission of the GOS phosphor. The filter also has a sharp short-pass cut-off at about 553

NM, that blue shifts at about 0.6 NM per angular degree of incidence to optimize optical gain.

Glass support 210 should be reasonably flat, clear, and free of severe defects. The thickness of support 210 can be 2 millimeters. The opposite side 280 of glass support 210 is coated with an anti-reflective layer (such as Magnesium Fluoride, green optimized) to increase transmittance and reduce optical artifacts to ensure that the large dynamic range of the phosphor emittance is captured.

Figure 13:
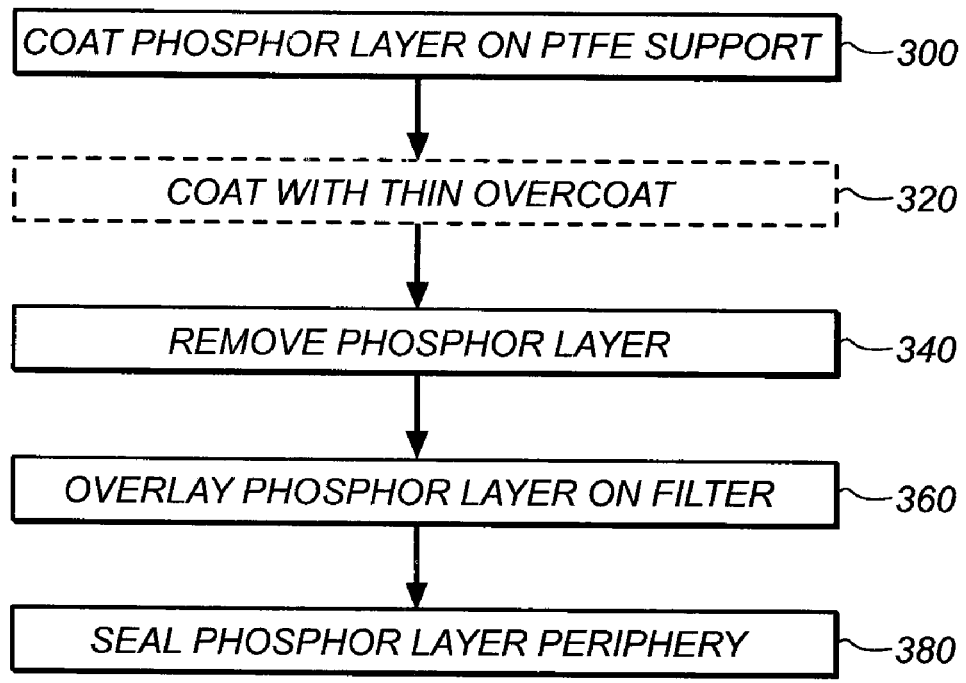
FIG. 13 is a flow diagram of a method for making a phosphor plate of FIG. 12.

FIG. 13 shows steps of a method of producing phosphor layer 240. In step 300, a mixture of GOS:Tb in a binder is coated on a polytetrafluoroethylene (PTFE) support. The PTFE support enables release of the coated phosphor layer from the PTFE support and subsequent use of the phosphor layer without support, since conventional supporting materials are an optical burden to phosphor performance. For the thin phosphor layer 240, at step 320 an ultra thin (about 0.5 g/ft2, 0.5 µm thick) layer of cellulose acetate overcoat can be applied to offer improved handling characteristics of the thin phosphor layer and to provide greater environmental protection to the underlying optical filter. At step 340, the phosphor layer is removed from the PFTE support. At step 360, the thin phosphor layer overcoated side is overlayed on interference filter 220. Clean assembly of the thin phosphor layer 240 and filter 220 assures an optical boundary that optimizes management of phosphor light output into the camera of the lens/camera system. Optical coupling of layer 240 and filter 220 is not necessary, since performance reduction may result. At step 380, layer 240 can be sealed around its periphery and around the periphery of filter 220 for mechanical stability and further protection of the critical optical boundary against environmental (e.g., moisture) intrusion.

Advantages of the present invention include: provides anatomical localization of molecular imaging agent signals in small animals, organs, and tissues; provides precise co-registration of anatomical x-ray images with optical molecular and radio isotopic images using one system; promotes improved understanding of imaging agent's biodistribution through combined use of time lapse molecular imaging with x-ray imaging; and allows simple switching between multi-wavelength fluorescence, luminescence, radio-isotopic, and x-ray imaging modalities without moving the object/sample.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 electronic imaging system
12 light source
14 optical compartment
16 mirror
18 lens/camera system
20 communication/computer control system
22 monitor
100 imaging system of the present invention
102 x-ray source
104 sample object stage
106 epi-illumination; fiber optics
108 sample environment
110 access means/member
120 frame
122 support sheet
125 phosphor plate
126 optical platen
128 protective layer
130 phosphor layer
132 optical layer
134 support plate; glass
136 air gap/void
138 air gap/void

What is claimed is:

1. An imaging system for imaging an object, comprising:
a support member adapted to receive the object in an immobilized state;
an imaging unit;
for imaging the immobilized object in a first imaging mode to capture a first image, the first imaging mode being selected from the group consisting of: x-ray mode and radio isotope mode; and
for imaging the immobilized object in a second imaging mode that uses light from the immobilized object, different from the first imaging mode, to capture a second image, the second imaging mode being selected from the group consisting of: bright-field mode, fluorescence mode, and luminescence mode;
a movable phosphor plate to transduce ionizing radiation to visible light, the phosphor plate being mounted to be moved, without moving the immobilized object and the support member, between
a first position proximate the support member for and during capture of the first image and
a second position not proximate the support member during capture of the second image; and
a capture system for capturing either the first image or the second image of the object.

2. An imaging system for imaging an object, comprising:
a support member adapted to receive the object in an immobilized state;
an imaging unit:
for imaging the immobilized object in a first imaging mode to capture a first image, the first imaging mode being selected from the group consisting of: x-ray imaging mode and isotope imaging mode; and
for imaging the immobilized object in a second imaging mode that uses light from the object to capture a second image, the second imaging mode being selected from the group consisting of: bright-field imaging mode and dark-field imaging mode;
a movable phosphor plate mounted to be disposed in a first position proximate the support member when capturing the first image;
means for removing the phosphor plate from the first position proximate the support member, after capturing the first image and without moving the immobilized object and the support member, and for moving the phosphor plate to a second position not proximate the support member prior to capturing the second image; and
a capture system for capturing either the first image or the second image of the object.

3. A method of imaging an object, comprising the steps of:
providing a support member adapted to receive the object in an immobilized state;
providing a phosphor plate adapted to be disposed proximate the support member when capturing a first image;
disposing the phosphor plate proximate the support member;

imaging the immobilized object in a first imaging mode to capture the first image, the first imaging mode being selected from the group consisting of: x-ray mode and radio isotope mode;

removing the phosphor plate from proximate the support member, after capturing the first image and without moving the immobilized object and the support member; and with the phosphor plate removed from proximate the support member, imaging the immobilized object in a second imaging mode that uses light from the object to capture a second image, the second imaging mode being selected from the group consisting of: bright-field mode and dark-field mode.

4. A method of imaging an object, comprising the steps of:

providing a support member adapted to receive the object in an immobilized state;

providing a phosphor plate movable relative to the support member, without moving the immobilized object and the support member, between a first position wherein the phosphor plate is in optical registration with the support member and a second position wherein the phosphor plate is not in optical registration with the support member;

disposing the phosphor plate in the first position;

capturing a first, x-ray image or a first, radio isotopic image of the immobilized object when the phosphor plate is disposed in the first position;

moving the phosphor plate to the second position; and using light from the object, capturing a second, dark-field image or a second, bright-field image of the immobilized object when the phosphor plate is disposed in the second position.

5. The imaging system of claim 1, further comprising an image merging unit for generating a third image by merging the first and second images.

6. The imaging system of claim 1, further comprising multiple optical elements to enable the location of a common focal plane shared by the first and second imaging modes.

7. The imaging system of claim 2, further comprising an image merging unit for generating a third image by merging the first and second images.

8. The imaging system of claim 2, further comprising multiple optical elements to enable the location of a common focal plane shared by the first and second imaging modes.

9. The method of claim 3, further comprising the step of generating a third image by merging the first and second images.

10. The method of claim 4, further comprising the steps of:

generating a third image by merging the first and second images; and displaying, transmitting, processing, or printing, the third image.

* * * * *

UNITED STATES PATENT AND TRADEMARK OFFICE
CERTIFICATE OF CORRECTION

PATENT NO. : 7,734,325 B2  Page 1 of 1
APPLICATION NO. : 11/221530
DATED : June 8, 2010
INVENTOR(S) : Douglas L. Vizard et al.

It is certified that error appears in the above-identified patent and that said Letters Patent is hereby corrected as shown below:

Column 10, line 15, claim 1    Please replace "unit;" with --unit:--
Column 10, line 34, claim 1    Please remove indentation of the line "a capture system ..."

Signed and Sealed this

Seventeenth Day of August, 2010

David J. Kappos
*Director of the United States Patent and Trademark Office*

(12) INTER PARTES REEXAMINATION CERTIFICATE (0372nd)
United States Patent
Vizard et al.

(10) Number: US 7,734,325 C1
(45) Certificate Issued: Apr. 17, 2012

(54) APPARATUS AND METHOD FOR MULTI-MODAL IMAGING

(75) Inventors: Douglas L. Vizard, Durham, CT (US); Joel N. Helfer, Cheshire, CT (US); George Brocksieper, Guilford, CT (US); William E. Mclaughlin, Guilford, CT (US)

(73) Assignee: Carestream Health, Inc., Rochester, NY (US)

Reexamination Request:
No. 95/001,379, Jun. 9, 2010

Reexamination Certificate for:
Patent No.: 7,734,325
Issued: Jun. 8, 2010
Appl. No.: 11/221,530
Filed: Sep. 8, 2005

Certificate of Correction issued Aug. 17, 2010.

Related U.S. Application Data
(60) Provisional application No. 60/611,841, filed on Sep. 21, 2004.

(51) Int. Cl.
*A61B 6/00* (2006.01)

(52) U.S. Cl. .................. 600/407; 600/425; 600/436; 600/476; 378/51; 382/131; 250/339.06; 250/336.01; 250/367

(58) Field of Classification Search .................. None
See application file for complete search history.

(56) References Cited

To view the complete listing of prior art documents cited during the proceeding for Reexamination Control Number 95/001,379, please refer to the USPTO's public Patent Application Information Retrieval (PAIR) system under the Display References tab.

*Primary Examiner* — Jeffrey R. Jastrzab

(57) ABSTRACT

An imaging system for imaging an object. The imaging system includes a support member adapted to receive the object in an immobilized state. The system also includes first means for imaging the immobilized object in a first imaging mode to capture a first image, and second means for imaging the immobilized object in a second imaging mode, different from the first imaging mode, to capture a second image. The first imaging mode is selected from the group: x-ray mode and radio isotopic mode. The second imaging mode is selected from the group: bright-field mode and dark-field mode. A removable phosphor screen is employed when the first image is captured and not employed when the second image is captured. The phosphor screen is adapted to transduce ionizing radiation to visible light. The phosphor screen is adapted to be removable without moving the immobilized object. The system can further include means for generating a third image comprised of the first and second image.

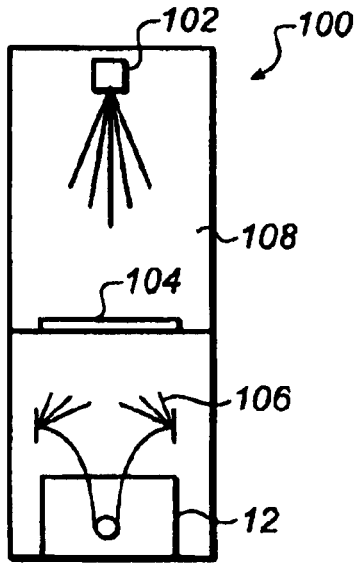
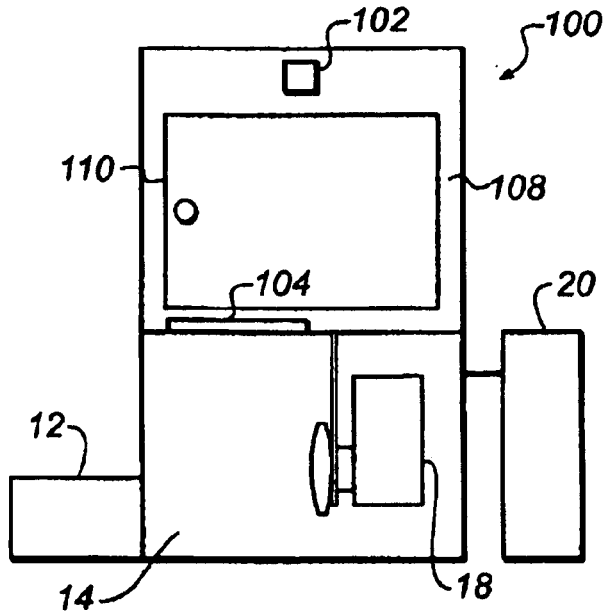

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-10 is confirmed.

* * * * *